United States Patent
Chen et al.

(10) Patent No.: US 7,663,383 B2
(45) Date of Patent: Feb. 16, 2010

(54) METHOD FOR DETECTION AND ANALYSIS OF IMPURITY CONTENT IN REFINED METALLURGICAL SILICON

(75) Inventors: Genmao Chen, Toronto, CA (US); Jiang Peng, Suzhou (CN)

(73) Assignee: CSI Cells Co. Ltd., Suzhou (CN)

( * ) Notice: Subject to any disclaimer, the term of this patent is extended or adjusted under 35 U.S.C. 154(b) by 0 days.

(21) Appl. No.: 12/286,910

(22) Filed: Oct. 3, 2008

(65) Prior Publication Data

US 2009/0091339 A1   Apr. 9, 2009

(30) Foreign Application Priority Data

Oct. 8, 2007   (CN) .................. 2007 1 0132843

(51) Int. Cl.
  *G01N 27/04*   (2006.01)
  *G01R 31/26*   (2006.01)
(52) U.S. Cl. ................. 324/719; 324/717; 324/765; 423/348
(58) Field of Classification Search ............ 324/715, 324/705, 719, 717
  See application file for complete search history.

(56) References Cited

U.S. PATENT DOCUMENTS 3,628,137 A * 12/1971 Mazur ................. 324/717
5,298,860 A * 3/1994 Kato ..................... 324/767
5,585,734 A * 12/1996 Meuris et al. ........... 324/719
6,201,401 B1 * 3/2001 Hellemans et al. ....... 324/719
6,313,648 B1 * 11/2001 Syo ..................... 324/719

* cited by examiner

*Primary Examiner*—Timothy J Dole
*Assistant Examiner*—John Zhu
(74) *Attorney, Agent, or Firm*—Fulwider Patton LLP

(57) ABSTRACT

A method for detection and analysis of impurity content of refined metallurgical silicon includes: (1) select the measuring points on the crystal rods or crystal ingots along the crystallization direction, measuring the resistivity at each measuring point and acquire the measured value of resistivity according to the distribution of crystallized fraction; (2) get the estimated value of the content of boron and phosphorus at each measuring point and calculate the estimated net redundant carrier concentration and the measured value of resistivity; (3) compare the estimated value of net redundant carrier concentration with that of the measured value, and adjust the estimated value of impurity content in the silicon material to get the new estimated net redundant carrier concentration, and use regression analysis to determine the impurity content distribution of boron and phosphorus; (4) get the average impurity content of boron and phosphorus in the silicon material according to the distribution status of impurity based on all the measuring points. This invention can detect the impurity contents of boron and phosphorus in refined metallurgical silicon, while the operation is simple, low-cost and suitable for industrial applications.

1 Claim, No Drawings

METHOD FOR DETECTION AND ANALYSIS OF IMPURITY CONTENT IN REFINED METALLURGICAL SILICON

CROSS-REFERENCES TO RELATED APPLICATIONS

This application claims priority from Chinese Patent Application Number 200710132843.7, filed Oct. 8, 2007.

BACKGROUND

This invention relates generally to a method for detection and analysis of an impurity content in silicon material, and more particularly to a method for detection and analysis of an impurity content in refined metallurgical silicon.

As the world's population become more and more aware of the problems of limited energy sources and environment pollution, the utilization of solar energy has changed from the research stage into industrialization. Solar photovoltaic technology has drawn universal attention, and silicon solar cells have begun to be widely used.

Conventional silicon cell wafers are made on P-type semiconductor substrates of silicon. The P-type wafer is made by doping of boron (0.02~0.25 ppmw) into ultra-pure silicon materials (better than 8N), so after the crystal growth, the resistivity is controlled within the range of 0.5~5 Ω.cm. A silicon wafer produced this way has a very high purity and the contents of unwanted impurities can be largely neglected. However, the price of silicon cells using ultra-pure silicon wafers is very expensive, which is a major hurdle that limits wider application of these types of solar cells.

Refined metallurgical silicon is a new type of low-cost silicon solar cell material. Its purity content is 2~3 N lower than conventional solar cell grade silicon material, that is, only about 5~6 N as compared to 8+N. Impurities of boron in refined metallurgical silicon is as high as 1~2 ppmw, and the content of phosphorus is also quite high, generally in the range of 3~12 ppmw. Boron is a P-type impurity, while phosphorus is an N-type impurity, so the refined metallurgical silicon is a kind of impurity compensation material. In the purification process of refined metallurgical silicon material, a commonly used method is directional crystallization. As the segregation coefficient of boron is 0.8, boron as an impurity will be distributed evenly in the material. Conversely, the segregation coefficient of phosphorus in metallurgical silicon is relatively smaller at about 0.33, making phosphorus as an impurity in refined metallurgical silicon unevenly distributed, and the content of phosphorus shows an exponential growth from one end of the crystal to the other end.

Conventional methods for detection and analysis of impurity contents includes glow discharge mass spectrometry (GDMS) and plasma mass spectrometry (ICP-MS). When used in the detection of impurities in refined metallurgical silicon, these two methods both have the following shortcomings: (1) one can only detect samples of about 1 g, and the distribution of impurities vary significantly, and therefore, it is very difficult to determine an accurate average content level of impurities in a large amount of the refined metallurgical silicon (such as a crystal ingot casting of 240 kg in a furnace); and (2) both conventional methods require expensive equipment, and the preparation of the sample is very complicated, so the cost of using a multi-point sampling detection method is too high and a multi-point sampling detection method could not be practically applied to actual production.

For these reasons, there are no known methods to accurately control the doping and the resistivity when using refined metallurgical silicon to cast crystal ingots for solar cells, leading to very low yield.

Thus, if one can provide a detection and analysis method that accurately detects the impurity content in a large quantity of refined metallurgical silicon material, it would be conducive to determining the doping in the course of making solar cells, so as to control the resistivity and improve the yield.

SUMMARY OF THE INVENTION

The object of the present invention is to provide a method for detection and analysis of impurities in refined metallurgical silicon, so as to simply and accurately analyze the average impurity of phosphorus and boron in large amounts of refined metallurgical silicon.

This object is achieved according to the technical solution described below in which a method for detection and analysis of the impurity content of refined metallurgical silicon is described, comprising:

(1) selecting a plurality of measuring points along the crystallization direction on a specimen of metallurgical silicon selected from a crystal rod and a crystal ingot, with a distance between two adjacent measuring points selected to be no more than 2 cm on the crystal rod, and no more than 1 cm on the crystal ingot, where a ratio of a weight from a starting point to each measuring point of the crystal rod or the crystal ingot and a material weight of the crystal rod or the crystal ingot is called a "crystallized fraction", and measuring a resistivity at each measuring point and acquiring a measured value of resistivity according to a distribution of crystallized fraction;

(2) determining an estimated value of a content of boron and a content of phosphorus at each measuring point based on an estimated value of impurity content as well as a segregate coefficient of original silicon material, and calculating an estimated net redundant carrier concentration and then calculating a measured value of net redundant carrier concentration according to a measured value of resistivity at every measuring point;

(3) comparing the estimated value of net redundant carrier concentration with the measured value, and adjusting the estimated value according to an exponential segregation of each point as well as the crystallized fraction to get a new estimated net redundant carrier concentration, and repeating the above steps and use regression analysis to determine the impurity content distribution of boron and phosphorus, so that an average square of a difference of the estimated value and the measured value of the net redundant carrier concentration is less than 0.01; and (4) determining an average impurity content of boron and phosphorus in the silicon material according to a distribution status of impurity based on all the measuring points.

In above technical solution, said crystal rods are made by pulling process from mono-crystalline furnace, while said crystal ingots are made by casting process from casting furnace.

DETAILED DESCRIPTION OF THE PREFERRED EMBODIMENTS

This invention will be best understood with reference to the following description of example embodiments:

Example

In a 60 $C_Z$ crystal furnace with 35 kg of refined metallurgical silicon, a straight pulling process for mono-crystallized silicon is used to produce a refined metallurgical silicon rod, and the above-described simulation analysis of impurity content of phosphorus and boron is employed.

Fifty-six measuring points are selected along the direction of crystallization, and the crystallized fraction of each point is shown in Table 1. The resistivity ρ at each point is measured, and then formula (4) is used to calculate the $N_{CC}$ at each point to obtain a group of distribution data. Then formulae (1) and (2) are applied, and crystallized fraction F is determined to obtain the function of $C_B$ and $C_P$ with relation to F, which is $C_B(F)$ and $C_P(F)$, and then formula (3) is used to get the estimated distribution data.

The formulas are shown below:

$$C_B(F) = S_B \cdot C_{B0}(1-F)^{(S_B-1)} \quad (1)$$

$$C_P(F) = S_P \cdot C_{P0}(1-F)^{(S_P-1)} \quad (2)$$

$$N_{CC} = (C_B - C_P) \times 5 \times 10^{17}/cm^3 \quad (3)$$

$$\rho = N_{CC} \cdot q \mu \quad (4)$$

Here, F stands for the crystallized fraction, that is, the ratio between the weight from the starting point to each measuring point of crystal rod or crystal ingot and the material weight of the whole crystal rod or ingot. This value is always between 0 to 1; $C_B$ (F) and $C_P$ (F) respectively stand for the estimated values of boron and phosphorus at the measuring point where the crystallized fraction is F; $C_{B0}$ and $C_{P0}$ respectively stand for the estimated average values of impurity contents of boron and phosphorus in the material to be inspected; $S_B$ and $S_P$ respectively stand for the segregation coefficients of boron and phosphorus in silicon, which are 0.8 and 0.33 respectively; $N_{CC}$ is the net redundant carrier density; ρ is the resistivity along the direction of crystal; q is the quantity of electric charge of the carrier; and μ is the carrier's mobility.

In this example, all groups of data shown in Table 1 below, through regression analysis to simulate, yields values of $C_{B0}$ and $C_{P0}$ of 2.39 ppma and 3.1224 ppma respectively, which are the average impurity contents in refined metallurgical silicon.

TABLE 1

| F | ρ | $N_{CC}$(E17) | $C_P$ | $C_B$ | $N'_{CC}$(E17) | Δx |
|---|---|---|---|---|---|---|
| 0.033 | 0.43 | 0.38 | 1.12 | 1.92 | 0.40 | 0.00057592 |
| 0.058 | 0.43 | 0.38 | 1.14 | 1.94 | 0.40 | 0.000378845 |
| 0.12 | 0.43 | 0.38 | 1.19 | 1.96 | 0.39 | 4.93513E-05 |
| 0.145 | 0.425 | 0.385 | 1.21 | 1.97 | 0.38 | 1.24836E-05 |
| 0.17 | 0.46 | 0.35 | 1.23 | 1.98 | 0.38 | 0.000653105 |
| 0.195 | 0.46 | 0.35 | 1.26 | 2.00 | 0.37 | 0.000370973 |
| 0.22 | 0.46 | 0.35 | 1.28 | 2.01 | 0.36 | 0.000157386 |
| 0.245 | 0.48 | 0.34 | 1.31 | 2.02 | 0.36 | 0.00023623 |
| 0.27 | 0.49 | 0.33 | 1.34 | 2.04 | 0.35 | 0.000312882 |
| 0.3013 | 0.55 | 0.28 | 1.38 | 2.05 | 0.34 | 0.003280881 |
| 0.3638 | 0.62 | 0.235 | 1.47 | 2.09 | 0.31 | 0.006144486 |
| 0.3893 | 0.66 | 0.225 | 1.51 | 2.11 | 0.30 | 0.005964243 |
| 0.4394 | 0.72 | 0.205 | 1.59 | 2.15 | 0.28 | 0.00523738 |
| 0.4644 | 0.88 | 0.165 | 1.64 | 2.17 | 0.26 | 0.009653307 |
| 0.4957 | 0.9 | 0.16 | 1.71 | 2.19 | 0.24 | 0.006996686 |
| 0.5075 | 1 | 0.145 | 1.73 | 2.20 | 0.24 | 0.008213073 |
| 0.52 | 1.1 | 0.13 | 1.76 | 2.21 | 0.23 | 0.009353465 |
| 0.5325 | 1.2 | 0.12 | 1.79 | 2.23 | 0.22 | 0.009475104 |

TABLE 1-continued

| F | ρ | $N_{CC}$(E17) | $C_P$ | $C_B$ | $N'_{CC}$(E17) | Δx |
|---|---|---|---|---|---|---|
| 0.57 | 1.3 | 0.1 | 1.89 | 2.26 | 0.19 | 0.007410072 |
| 0.5825 | 1.5 | 0.093 | 1.93 | 2.28 | 0.17 | 0.00663728 |
| 0.595 | 1.6 | 0.087 | 1.97 | 2.29 | 0.16 | 0.00565125 |
| 0.6075 | 1.9 | 0.075 | 2.01 | 2.31 | 0.15 | 0.005496258 |
| 0.611 | 2.5 | 0.055 | 2.02 | 2.31 | 0.15 | 0.008161999 |
| 0.6235 | 3 | 0.045 | 2.06 | 2.32 | 0.13 | 0.007439628 |
| 0.6423 | 7 | 0.019 | 2.13 | 2.35 | 0.11 | 0.007977192 |
| 0.7225 | −3.8 | −0.012 | 2.51 | 2.47 | −0.02 | 9.54327E-05 |
| 0.735 | −2.1 | −0.022 | 2.59 | 2.49 | −0.05 | 0.000705561 |
| 0.7475 | −1.5 | −0.032 | 2.67 | 2.52 | −0.08 | 0.002096356 |
| 0.76 | −1 | −0.049 | 2.76 | 2.54 | −0.11 | 0.003695244 |
| 0.7725 | −0.7 | −0.071 | 2.86 | 2.57 | −0.14 | 0.00547454 |
| 0.82 | −0.35 | −0.158 | 3.33 | 2.69 | −0.32 | 0.025777198 |
| 0.8575 | −0.2 | −0.3 | 3.88 | 2.82 | −0.53 | 0.051650242 |
| 0.9075 | −0.1 | −0.8 | 5.14 | 3.08 | −1.03 | 0.052266102 |

We claim:

1. A method for detection and analysis of an impurity content of refined metallurgical silicon, comprising:
   (1) selecting a plurality of measuring points along a crystallization direction on a specimen of metallurgical silicon selected from a crystal rod and a crystal ingot, with a distance between two adjacent measuring points selected to be no more than 2 cm on the crystal rod, and no more than 1 cm on the crystal ingot, where a ratio of a weight from a starting point to each measuring point of the crystal rod or the crystal ingot and a material weight of the crystal rod or the crystal ingot is called a "crystallized fraction", and measuring a resistivity at each measuring point and acquiring a measured value of resistivity according to a distribution of crystallized fraction;
   (2) determining an estimated value of a content of boron and a content of phosphorus at each measuring point based on an estimated value of impurity content as well as a segregate coefficient of original silicon material, and calculating an estimated net redundant carrier concentration and then calculating a measured value of net redundant carrier concentration according to a measured value of resistivity at every measuring point;
   (3) comparing the estimated value of net redundant carrier concentration with the measured value, and adjusting the estimated value according to an exponential segregation of each point as well as the crystallized fraction to get a new estimated net redundant carrier concentration, and repeating the above steps and use regression analysis to determine the impurity content distribution of boron and phosphorus, so that an average square of a difference of the estimated value and the measured value of the net redundant carrier concentration is less than 0.01; and
   (4) determining an average impurity content of boron and phosphorus in the silicon material according to a distribution status of impurity based on all the measuring points.

* * * * *

UNITED STATES PATENT AND TRADEMARK OFFICE
CERTIFICATE OF CORRECTION

| | | |
|---|---|---|
| PATENT NO. | : 7,663,383 B2 | Page 1 of 1 |
| APPLICATION NO. | : 12/286910 | |
| DATED | : February 16, 2010 | |
| INVENTOR(S) | : Genmao Chen et al. | |

It is certified that error appears in the above-identified patent and that said Letters Patent is hereby corrected as shown below:

Title Page, Item (75)

Delete "Toronto, CA (US)" and insert --Toronto, Canada--

Title Page, Item (30):

Delete "2007 1 0132843" and insert --2007 1 0132843.7--

Signed and Sealed this

Twenty-first Day of September, 2010

David J. Kappos
*Director of the United States Patent and Trademark Office*